US012565514B2

(12) United States Patent
Okazoe et al.

(10) Patent No.: US 12,565,514 B2
(45) Date of Patent: Mar. 3, 2026

(54) NUCLEIC ACID CONTAINING PERFLUOROALKYL GROUP, AND METHOD FOR ITS PRODUCTION

(71) Applicants: AGC Inc., Tokyo (JP); THE UNIVERSITY OF TOKYO, Tokyo (JP)

(72) Inventors: Takashi Okazoe, Tokyo (JP); Yuichiro Ishibashi, Tokyo (JP); Akimitsu Okamoto, Tokyo (JP); Kunihiko Morihiro, Tokyo (JP); Kohsuke Aikawa, Tokyo (JP); Honoka Watanabe, Tokyo (JP)

(73) Assignees: AGC INC., Tokyo (JP); THE UNIVERSITY OF TOKYO, Tokyo (JP)

( * ) Notice: Subject to any disclaimer, the term of this patent is extended or adjusted under 35 U.S.C. 154(b) by 1021 days.

(21) Appl. No.: 17/699,044

(22) Filed: Mar. 18, 2022

(65) Prior Publication Data

US 2022/0235091 A1 Jul. 28, 2022

Related U.S. Application Data

(63) Continuation of application No. PCT/JP2020/036392, filed on Sep. 25, 2020.

(30) Foreign Application Priority Data

Sep. 27, 2019 (JP) ................................ 2019-177622

(51) Int. Cl.
*C07H 21/04* (2006.01)

(52) U.S. Cl.
CPC .................................. *C07H 21/04* (2013.01)

(58) Field of Classification Search
CPC ...... A61K 31/7088; A61P 43/00; C07H 21/04
See application file for complete search history.

(56) References Cited

U.S. PATENT DOCUMENTS

| | | | | |
|---|---|---|---|---|
| 12,251,446 B2 * | 3/2025 | Uehara | A61K 47/60 | |
| 2014/0065223 A1 * | 3/2014 | Schafer | A61K 47/54 | 536/23.1 |

FOREIGN PATENT DOCUMENTS

| | | |
|---|---|---|
| JP | 2006-321797 A | 11/2006 |
| JP | 2014-510743 A | 5/2014 |
| WO | WO-00/056694 A1 | 9/2000 |
| WO | WO-2011/036557 A1 | 3/2011 |
| WO | WO-2012/130941 A2 | 10/2012 |
| WO | WO-2017/212006 A1 | 12/2017 |

OTHER PUBLICATIONS

Cai et al., "Bioreducible Fluorinated Peptide Dendrimers Capable of Circumventing Various Physiological Barriers for Highly Efficient and Safe Gene Delivery," ACS Applied Materials and Interfaces, vol. 8, 2016, pp. 5821-5832.
Ellipilli et al., "Perfluoroalkylchain conjugation as a new tactic for enhancing cell permeability of peptide nucleic acids (PNAs) via reducing the nanoparticle size," Chemical Communications, vol. 52, 2016, pp. 521-524.
Godeau et al., "Fluorocarbon oligonucleotide conjugates for nucleic acids delivery," Medicinal Chemistry Communications, vol. 1, 2010, pp. 76-78.
Metelev et al., "Fluorocarbons Enhance Intracellular Delivery of Short STAT3-sensors and Enable Specific Imaging," Theranostics, vol. 7, Issue 13, 2017, pp. 3354-3368.
Rochambeau et al., "DNA-Teflon" sequence-controlled polymers, Polymer Chemistry, vol. 7, 2016, pp. 4998-5003.
Watanabe et al., "Fluorine-containing oligonucleotides for cell membrane permeability," Proceedings of the 3rd Annual Meeting of Japan Society of Nucleic Acids Chemistry, vol. 46, No. 3, 2019, pp. 280-281.
Zhang et al., "Perfluorocarbon-based nanomedicine: emerging strategy for diagnosis and treatment of diseases," MRS Communications, vol. 8, 2018, pp. 303-313.
International Searching Authority, "International Search Report," issued in connection with International Patent Application No. PCT/JP2020/036392, dated Dec. 1, 2020.
International Searching Authority, "Written Opinion," issued in connection with International Patent Application No. PCT/JP2020/036392, dated Dec. 1, 2020.

* cited by examiner

*Primary Examiner* — Pancham Bakshi
(74) *Attorney, Agent, or Firm* — Foley & Lardner LLP

(57) ABSTRACT

To provide a nucleic acid excellent in cell membrane permeability and a method for its production.

A nucleic acid containing a $C_{2-10}$ perfluoroalkyl group having from 1 to 5 ether-bonding oxygen atoms between carbon atoms; said nucleic acid wherein said perfluoroalkyl group is directly or indirectly bonded to the 5'- or 3'-end of the nucleic acid, or said perfluoroalkyl group is indirectly introduced between two nucleotides; or a nucleic acid medicine comprising, as an active ingredient, a nucleic acid containing a $C_{2-10}$ perfluoroalkyl group, which may have from 1 to 5 ether-bonding oxygen atoms between carbon atoms.

6 Claims, 4 Drawing Sheets

Specification includes a Sequence Listing.

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthesized DNA

<400> SEQUENCE: 1
tttttcagtt gaccatata 19

<210> SEQ ID NO 2
<211> LENGTH: 19
<212> TYPE: DNA

-continued

```
<213> ORGANISM: Artificial Sequence
<220> FEATURE:
<223> OTHER INFORMATION: Description of Artificial Sequence: Synthesized
      rDNA

<400> SEQUENCE: 2

tatatggtca actgaaaaa                                                19


<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthesized
      RNA

<400> SEQUENCE: 3

uuuuucaguu gaccauaua                                                19


<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthesized
      rRNA

<400> SEQUENCE: 4

uauaugguca acugaaaaa                                                19
```

NUCLEIC ACID CONTAINING PERFLUOROALKYL GROUP, AND METHOD FOR ITS PRODUCTION

CROSS-REFERENCE TO RELATED APPLICATIONS

This application is a Bypass Continuation of PCT Application No. PCT/JP2020/036392, filed on Sep. 25, 2020, which is based upon and claims the benefit of priority from Japanese Patent Application No. 2019-177622 filed on Sep. 27, 2019. The contents of those applications are incorporated herein by reference in their entireties.

SEQUENCE LISTING

The instant application contains a Sequence Listing which has been submitted electronically in ASCII format and is hereby incorporated by reference in its entirety. Said ASCII copy, created on Apr. 6, 2022, is named 086524-0183_SL.txt and is 1,251 bytes in size.

TECHNICAL FIELD

The present invention relates to a nucleic acid having a perfluoroalkyl group introduced, and a method for its production.

BACKGROUND ART

Antibody drugs are excellent as therapeutic agents for cancer and intractable diseases because they can be made to be drugs so long as antibodies can be prepared by using the immune system against proteins that cannot be targeted by low-molecular-weight drugs. Further, antibody drugs have such an advantage that specificity for target molecules is high and side effects are less. However, it is difficult for antibody drugs to pass through cell membranes and enter cells, whereby it difficult to use molecules other than those on the cell surface as target molecules.

Nucleic acid drugs using oligonucleotides are being studied as the next generation of drug discovery after antibody drugs. Nucleic acid drugs have such an advantage that specificity for target molecules is high and side effects are less. However, like antibody drugs, nucleic acid drugs also have low cell membrane permeability, whereby it is difficult for them to reach the target molecules in the cells. In particular, since siRNA is double-stranded, its molecular weight and negative charge are both larger than those of antisense RNA, and its cell membrane permeability is lower than that of antisense RNA, thus requiring drug delivery by a carrier. As drug delivery agents, ones using lipid nanoparticles (Patent Document 1) and ones using cationic polymer nanoparticles (Patent Document 2) are known. However, there are many things that need to be improved in view of the efficiency of cell membrane permeability and toxicity concerns.

On the other hand, compounds having polyfluorinated structures are known to be stable in vivo, have low toxicity and are excellent for cellular uptake and escape from endosomes (Non-Patent Document 1). It has been reported that taking advantage of this property, peptide dendrimers using lysine with perfluoroacylated amino groups on the side chain as the constituent amino acids can be used for gene delivery (Non-Patent Document 2). Further, the introduction of polyfluorinated structures into oligonucleotides or peptide nucleic acids as cell membrane-permeable moieties has also been investigated (Patent Document 3, and Non-Patent Documents 3 to 6).

PRIOR ART DOCUMENTS

Patent Documents

Patent Document 1: WO2011/036557
Patent Document 2: WO02017/212006
Patent Document 3: WO2012/130941
Patent Document 4: JP-A-2006-321797
Patent Document 5: WO2000/056694

Non-Patent Documents

Non-Patent Document 1: Zhang et al., MRS Communications, 2018, vol. 8, p. 303-313.
Non-Patent Document 2: Cai et al., ACS Applied Materials and Interfaces, 2016, vol. 8, p. 5821-5832.
Non-Patent Document 3: Godeau et al., Medicinal Chemistry Communications, 2010, vol. 1. p. 76-78.
Non-Patent Document 4: Ellipilli et al., Chemical Communications, 2016, vol. 52, p. 521-524.
Non-Patent Document 5: Rochambeau et al., Polymer Chemistry, 2016, vol. 7, p. 4998-5003.
Non-Patent Document 6: Metelev et al., Theranostics, 2017, vol. 7, p. 3354-3368.

DISCLOSURE OF INVENTION

Technical Problem

The purpose of the present invention is to provide a nucleic acid excellent in cell membrane permeability and a method for its production.

Solution to Problem

The present inventors have found that by introducing a perfluoroalkyl group, especially a perfluoroalkyl group having an ether-bonding oxygen atom, it is possible to improve the cell membrane permeability of a nucleic acid, and thus have accomplished the present invention.

That is, the present invention is as follows.

[1] A nucleic acid containing a $C_{2-10}$ perfluoroalkyl group having from 1 to 5 ether-bonding oxygen atoms between carbon atoms.

[2] The nucleic acid according to [1], wherein the perfluoroalkyl group is directly or indirectly bonded to the 5'- or 3'-end of the nucleic acid.

[3] The nucleic acid according to [1], wherein the perfluoroalkyl group is indirectly introduced between two nucleotides.

[4] The nucleic acid according to any one of [1] to [3], which has a structure represented by the following general formula (A1):

(A1)

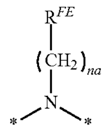

provided that the groups in the formula mean the following:

$R^{FE}$ is a $C_{2-10}$ perfluoroalkyl group having from 1 to 5 ether-bonding oxygen atoms between carbon atoms, na is an integer of from 1 to 10, and the black dots represent the bonding hands.

[5] The nucleic acid according to any one of [1] to [4], which is a cell membrane-permeable nucleic acid.

[6] A method for producing a nucleic acid containing a perfluoroalkyl group, in which a compound represented by the following general formula (A2) is used as a raw material, and a nucleic acid containing a perfluoroalkyl group as defined in any one of [1] to [5] is synthesized using phosphoramidite chemistry:

(A2)

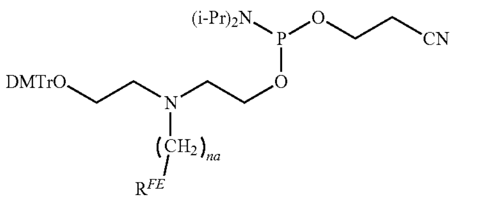

provided that the groups in the formula mean the following:

$R^{FE}$ is a $C_{2-10}$ perfluoroalkyl group having from 1 to 5 ether-bonding oxygen atoms between carbon atoms, na is an integer of from 1 to 10, DMTr is a 4,4'-dimethoxytriphenylmethyl group, and i-Pr is an isopropyl group.

[7] A nucleic acid medicine containing, as the active ingredient, a nucleic acid containing a $C_{2-10}$ perfluoroalkyl group which may have from 1 to 5 ether-bonding oxygen atoms between carbon atoms.

[8] A method for improving the cell membrane permeability of a nucleic acid, which comprises introducing a $C_{2-10}$ perfluoroalkyl group which may have from 1 to 5 ether-bonding oxygen atoms between carbon atoms, into a nucleic acid, to improve the cell membrane permeability.

[9] The method of improving the cell membrane permeability of a nucleic acid according to [8], wherein the perfluoroalkyl group is a group having from 1 to 5 ether-bonding oxygen atoms between carbon atoms.

[10] The method for improving the cell membrane permeability of a nucleic acid according to [8], wherein the perfluoroalkyl group is a group not having ether-bonding oxygen atoms between carbon atoms.

[11] The method for improving cell membrane permeability of a nucleic acid according to any one of [8] to [10], wherein the perfluoroalkyl group is directly or indirectly bonded to the 5'- or 3'-end of the nucleic acid.

Advantageous Effects of Invention

Further, the nucleic acid according to the present invention is excellent in cell membrane permeability since a perfluoroalkyl group has been introduced. For this reason, the nucleic acid is expected to be used in the pharmaceutical field as a bioactive substance.

According to the production method of the present invention, it is possible to produce a nucleic acid having a perfluoroalkyl group introduced.

DESCRIPTION OF EMBODIMENTS

Figure 1A:
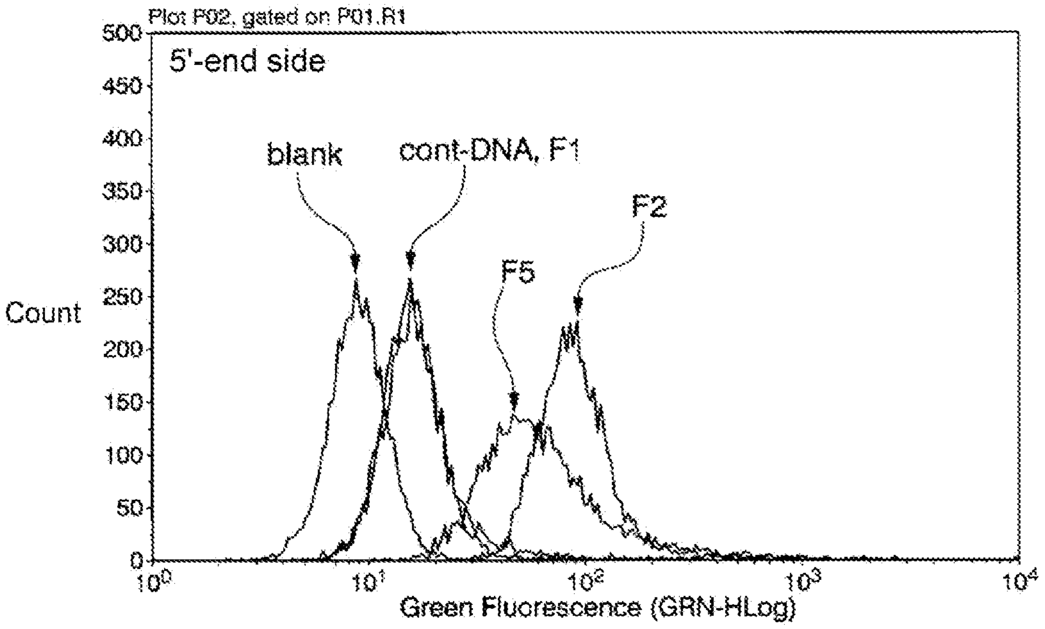
FIG. 1A is a graph showing the results of flow cytometry of cells having fluorescein-modified nucleic acids with N[$C_8$-PFC] modification at the 5'-end incorporated in Test Example 1.

In the present invention and the present specification, "nucleic acid" means a molecule having nucleotides bound by a phosphate diester bond. The nucleotides include not only natural nucleotides (naturally occurring nucleotides) such as DNA and RNA, but also artificial nucleotides that are modified from natural nucleotides and can be bonded to natural nucleotides by a phosphate diester bond. Artificial nucleotides include those in which the side chain of the natural nucleotide is modified with a functional group such as an amino group, those in which the hydroxy group at the 2' position of the ribose backbone is replaced with a methoxy group, a fluoro group, a methoxyethyl group, etc., phosphorothioate-type nucleotides (in which the oxygen atom of the phosphate group is replaced with a sulfur atom), morpholino-type nucleotides (ribose and deoxyribose are replaced with a morpholine ring), BNA (Bridged nucleic acid), HNA (Hexitol nucleic acid), LNA (Locked nucleic acid), PNA (Peptide nucleic acid), TNA (Threose nucleic acid), GNA (Glycerol nucleic acid), CeNA (Cyclohexenyl nucleic acid), etc. Further, "nucleic acid" includes any of the following: a molecule in which only one or more natural nucleotides, such as DNA or RNA, are bound by a phosphate diester bond; a molecule in which one or more natural nucleotides and one or more artificial nucleotides are bound by a phosphate diester bond; or a molecule in which only one or more artificial nucleotides are bound by a phosphate diester bond.

In the present invention and the present specification, "$C_{p1-p2}$" (p1 and p2 are positive integers satisfying p1<p2) means a group in which the number of carbon atoms is from p1 to p2.

In the present invention and the present specification, a "$C_{1-10}$ alkyl group" is an alkyl group having from 1 to 10 carbon atoms and may be either a straight chain or a branched chain. A "$C_{2-10}$ alkyl group" is an alkyl group having from 2 to 10 carbon atoms and may be either a straight chain or a branched chain. Examples of the "$C_{1-10}$ alkyl group" include a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group, a heptyl group, an octyl group, a nonyl group, a decyl group, etc.

In the present invention and the present specification, a "$C_{1-6}$ alkyl group" is an alkyl group having from 1 to 6 carbon atoms and may be either a straight chain or a branched chain. Examples of the $C_{1-6}$ alkyl group include a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group, etc.

In the present invention and the present specification, an "alkylene group" is a divalent group having two hydrogen atoms removed from a saturated hydrocarbon group, and may be either a straight chain or a branched chain. Examples of the alkylene group include a methylene group, an ethylene group, a trimethylene group, a tetramethylene group, a pentamethylene group, a hexamethylene group, a heptamethylene group, an octamethylene group, a nonamethylene group, a methylmethylene group, an ethylmethylene group, a methylethylene group, a methyl propylene group, an ethylethylene group, a dimethylmethylene group, a 1,2-dimethylethylene group, a 1,1-dimethylethylene group, a 1-ethylpropylene group, a 2-ethylpropylene group, a 1,2 dimethylpropylene group, a 2,2-dimethylpropylene group, a 1-propylpropylene group, a 2-propylpropylene group, a 1-methyl-1-ethylpropylene group, a 1-methyl-2-ethyl-propylene group, a 1-ethyl-2-methyl-propylene group, a 2-methyl-2-ethyl-propylene group, a 1-methylbutylene group, a 2-methylbutylene group, a 3-methylbutylene group, a 2-ethylbutylene group, a 1-methylpentylene group, a 2-ethylpentylene group, a 1-methylhexylene group, etc.

In the present invention and the present specification, a "$C_{1-10}$ perfluoroalkyl group" is a group in which all hydrogen atoms of a $C_{1-10}$ alkyl group have been replaced with fluorine atoms. Examples of the $C_{1-10}$ perfluoroalkyl group include a perfluoromethyl group, a perfluoroethyl group, a perfluoropropyl group, a perfluoroisopropyl group, a perfluorobutyl group, a perfluoroisobutyl group, a perfluorosec-butyl group, a perfluorotert-butyl group, a perfluoropentyl group, a perfluoroisopentyl group, a perfluoroneopentyl group, a perfluorotert-pentyl group, a perfluorohexyl group, a perfluoroheptyl group, a perfluorooctyl group, a perfluorononyl group, a perfluorodecyl group, etc.

In the present invention and the present specification, a "perfluoroalkylene group" is a group in which all hydrogen atoms of the alkylene group have been substituted with fluorine atoms. An example of the perfluoroalkylene group is a group in which all hydrogen atoms of the alkylene group listed above have been substituted with fluorine atoms.

In the present invention and the present specification, "ether-bonding oxygen atoms" are oxygen atoms whereby carbon atoms are bonded to each other, and do not include oxygen atoms in which oxygen atoms are linked together in series. The maximum number of ether-bonding oxygen atoms that an alkyl group of carbon number Nc (Nc is an integer of at least 2) can have is Nc-1. A "$C_{2-10}$ alkyl group having an ether-bonding oxygen atom between carbon atoms" is a group having at least one ether-bonding oxygen atom between carbon atoms of the $C_{1-10}$ alkyl group. Hereinafter, it may be referred to as an "ether bond-containing alkyl group".

In the present invention and the present specification, "a $C_{2-10}$ perfluoroalkyl group having an ether-bonding oxygen atom between carbon atoms" is a group in which all hydrogen atoms of an ether bond containing $C_{2-10}$ alkyl group having at least one ether-bonding oxygen atom between carbon atoms of the $C_{2-10}$ alkyl group are replaced by fluorine atoms. Hereafter, a "perfluoroalkyl group having an ether-bonding oxygen atom between carbon atoms" may be referred to as "ether bond-containing perfluoroalkyl group".

Further, in the following, a "compound n" refers to a compound represented by the formula (n).

<Nucleic Acid Containing an Ether Bond-containing Perfluoroalkyl Group>

The nucleic acid according to the present invention is a nucleic acid that contains a $C_{2-10}$ perfluoroalkyl group having from 1 to 5 ether-bonding oxygen atoms between carbon atoms. Since the nucleic acid contains the perfluoroalkyl group, it is expected to be used in the pharmaceutical field as a bioactive substance, similar to other fluorinated compounds.

The perfluoroalkyl group is not particularly limited, so long as it is a perfluoroalkyl group having from 2 to 10 carbon atoms and having from 1 to 5 ether-bonding oxygen atoms between carbon atoms. As the perfluoroalkyl group which the nucleic acid of the present invention has, for example, a group represented by any one of the following general formulae (F1) to (F3) is preferred.

$$—R^{F1}—O—R^{F2} \quad (F1)$$

$$—R^{F3}—(O—CF_2—CF_2—)n1\text{-}O—R^{F4} \quad (F2)$$

$$—R^{F5}—(O—CF_2—CF_2—CF_2—)n2\text{-}O—R^{F6} \quad (F3)$$

In the general formula (F1), $R^{F1}$ is a $C_{q1}$ perfluoroalkylene group, and $R^{F2}$ is a $C_{q2}$ perfluoroalkyl group. q1 and q2 are natural numbers such that the sum of the two becomes to be at least 2 and at most 10.

In the general formula (F2), $R^{F3}$ is a $C_{q3}$ perfluoroalkylene group, and $R^{F4}$ is a $C_{q4}$ perfluoroalkyl group. n1, q3 and q4 are natural numbers such that 2×n1+q3+q4 becomes to be at least 4 and at most 10.

In the general formula (F3), $R^{F5}$ is a $C_{q5}$ perfluoroalkylene group, and $R^{F6}$ is a $C_{q6}$ perfluoroalkyl group. n2, q5 and q6 are natural numbers such that 3×n2+q5+q6 becomes to be at least 5 and at most 10.

$R^{F1}$ in the general formula (F1), $R^{F3}$ in the general formula (F2) and $R^{F5}$ in the general formula (F3) may be a linear perfluoroalkylene group or a branched-chain perfluoroalkylene group. As $R^{F1}$, $R^{F3}$ and $R^{F5}$, a $C_{1-3}$ perfluoroalkylene group is preferred, a group in which all hydrogen atoms of a methylene group, an ethylene group, a methylmethylene group, an ethylmethylene group, a dimethylmethylene group or a methylethylene group are substituted with fluorine atoms is more preferred, and a group in which all hydrogen atoms of a methylene group, a methylmethylene group, an ethylmethylene group or a dimethylmethylene group are substituted with fluorine atoms is further preferred, and a group in which all hydrogen atoms of a methylene group or a methylmethylene group are substituted with fluorine atoms is still more preferred.

$R^{F2}$ in the general formula (F1), $R^{F4}$ in the general formula (F2) and $R^{F6}$ in the general formula (F3) may be a linear perfluoroalkyl group or a branched-chain perfluoroalkyl group. As $R^{F2}$, $R^{F4}$ and $R^{F6}$, a linear or branched-chain $C_{1-5}$ perfluoroalkyl group is preferred, a linear $C_{1-5}$ perfluoroalkyl group is more preferred, and a linear $C_{2-4}$ perfluoroalkyl group is further preferred.

As the perfluoroalkyl group, which the nucleic acid of the present invention has, preferred is a compound of the general formula (F1) in which $R^{F1}$ is a group in which all hydrogen atoms of a methylene group or a methylmethylene group are substituted with fluorine atoms, and $R^{F2}$ is a linear $C_{1-5}$ perfluoroalkyl group; a compound of the general formula (F2) in which $R^{F3}$ is a group in which all hydrogen atoms of a methylene group or a methylmethylene group are substituted with fluorine atoms, n1 is 1, 2 or 3, and $R^{F4}$ is a linear $C_{1-7}$ perfluoroalkyl group; or a compound of the general formula (F3) in which $R^{F5}$ is a group in which all hydrogen atoms of a methylene group or a methylmethylene group are substituted with fluorine atoms, n2 is 1 or 2, and $R^{F6}$ is a linear $C_{1-6}$ perfluoroalkyl group; and more preferred is a compound of the general formula (F1) in which $R^{F1}$ is a group in which all hydrogen atoms of a methylene group or a methylmethylene group are substituted with fluorine atoms, and $R^{F2}$ is a linear $C_{1-5}$ perfluoroalkyl group; a compound of the general formula (F2) in which $R^{F3}$ is a group in which all hydrogen atoms in a methylene group or a methylmethylene group are substituted with fluorine atoms, n1 is 1, and $R^{F4}$ is a linear $C_{1-6}$ perfluoroalkyl group; a compound of the general formula (F2) in which $R^{F3}$ is a group in which all hydrogen atoms of a methylene group or a methylmethylene group are substituted with fluorine atoms, n1 is 2, and $R^{F4}$ is a linear $C_{1-4}$ perfluoroalkyl group; a compound of the general formula (F2) in which $R^{F3}$ is a group in which all hydrogen atoms of a methylene group or a methylmethylene group are substituted with fluorine atoms, n1 is 3, and $R^{F4}$ is a linear $C_{1-3}$ perfluoroalkyl group; or a compound of the general formula (F3) in which $R^{F5}$ is a group in which all hydrogen atoms of a methylene group or a methylmethylene group are substituted with fluorine atoms, n2 is 1, and $R^{F6}$ is a linear $C_{1-6}$ perfluoroalkyl group.

In the present invention, as the ether bond-containing perfluoroalkyl group to be introduced into the nucleic acid, it is possible to use, for example, an ether bond-containing perfluoroalkyl group provided by a fluorine-containing compound described in Patent Document 4 or 5 together with its synthesis method.

In the nucleic acid of the present invention, the position where the ether bond-containing perfluoroalkyl group is introduced is not particularly limited, and it may be introduced at any site to such an extent that the function of the nucleic acid is not impaired. For example, the ether bond-containing perfluoroalkyl group may be directly or indirectly bonded to the 5'- or 3'-end of the nucleic acid, or may be introduced between two nucleotides. In a case where the ether bond-containing perfluoroalkyl group is indirectly introduced into the nucleic acid via a linking group, the linking group is not particularly limited so long as it does not impair the effect of the present invention, and an optional divalent or trivalent organic group may be used. The linking group may, for example, be an alkylene group, an alkenylene group, a carbonyl group, an amino group, an ether bond, a thioether bond, an ester bond, an amide bond, a polyethylene glycol group (PEG: $—(C_2H_4O)_n—$), a siloxane bond, a silyl ether bond, a sugar, or a peptide. Further, it is also possible to use, as a linking group, a group having two or three hydrogen atoms removed from a ring such as a pyrrole ring, a pyrazole ring, an imidazole ring, a triazole ring, a pyridine ring, a pyrimidine ring, a pyrazine ring, an oxazole ring, a thiazole ring, a furan ring, a thiophene ring or a benzene ring. Furthermore, these may be used in combination as appropriate.

In the nucleic acid of the present invention, the nucleic acid into which the ether bond-containing perfluoroalkyl group is introduced is not particularly limited, and may be a nucleic acid in which all the nucleotides contained are natural nucleotides, or may be a nucleic acid in which some or all of the nucleotides are artificial nucleotides. Further, it may be a single-stranded nucleic acid or a double-stranded nucleic acid. Examples of the nucleic acid include genomic DNA, cDNA, mRNA, microRNA, siRNA, antisense oligonucleotides, nucleic acid aptamers, decoy nucleic acids, and CpG (cytosine-phosphate-guanine) oligonucleotides. Further, it may also be an expression vector that expresses the target gene or siRNA in the cell.

In the nucleic acid of the present invention, the ether bond-containing perfluoroalkyl group can be introduced by various coupling reactions into the nucleic acid to which the group is to be introduced. For example, the ether bond-containing perfluoroalkyl group can be easily introduced into the nucleic acid by the phosphoramidite chemistry by using a phosphoramidite containing the ether bond-containing perfluoroalkyl group as a raw material. A general-purpose automated nucleic acid synthesizer utilizes the phosphoramidite chemistry. Therefore, by using a phosphoramidite containing the ether-bond containing perfluoroalkyl group as a raw material, nucleic acids having ether-bond containing perfluoroalkyl groups introduced at the desired positions to nucleic acids of various base sequences, can be easily synthesized by the automated synthesizer.

As the phosphoramidite containing the ether-bond containing perfluoroalkyl group, for example, among phosphoramidites generally used for nucleic acid synthesis, a compound in which the nucleoside moiety is replaced with an organic group containing an ether-bond containing perfluoroalkyl group may be mentioned. As such a compound, a compound represented by the following general formula (A2) may be mentioned.

(A2)

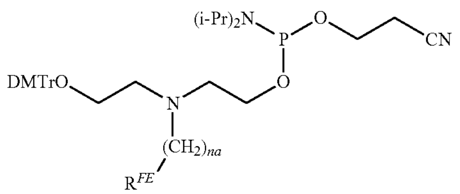

In the general formula (A2), $R^{FE}$ is the above-mentioned ether bond-containing perfluoroalkyl group. Further, na is an integer of from 1 to 10. i-Pr represents an isopropyl group, and DMTr represents a 4,4'-dimethoxytriphenylmethyl group.

The nucleic acid synthesized by the phosphoramidite chemistry using the compound (A2) has the structure of the following general formula (A1). In the general formula (A1), $R^{FE}$ is the above-mentioned ether bond-containing perfluoroalkyl group. Further, na is an integer of from 1 to 10. The black dots represent the bonding hands.

(A1)

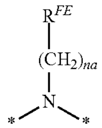

The synthesized nucleic acid of interest can be isolated and purified by various methods, such as ion chromatography, gel filtration chromatography, reversed-phase chromatography, normal-phase chromatography, etc.

The nucleic acid of the present invention may be one modified in various ways as long as the functions of the nucleic acid into which the ether-bond containing perfluoroalkyl group is introduced are not impaired and the effects of the present invention are not impaired. The modifications include glycosylation, lipid modification, peptide modification, etc.

The perfluorinated structure has a high affinity for the cell membrane. For this reason, the nucleic acid according to the present invention, in which the ether bond-containing perfluoroalkyl group is introduced, has better cell membrane permeability than a nucleic acid in which the group is not introduced. Taking advantage of this property, the nucleic acid of the present invention is particularly desirable as an active ingredient of a nucleic acid drug. For example, by introducing an ether bond-containing perfluoroalkyl group into a functional nucleic acid that exhibits some physiological activity when taken into a target cell in vivo, without impairing its function, it is possible to improve the efficiency for taking the functional nucleic acid into the target cell.

<Method for Improving Cell Membrane Permeability of Nucleic Acid>

By introducing a $C_{2-10}$ perfluoroalkyl group which may have from 1 to 5 ether-bonding oxygen atoms between carbon atoms, into a nucleic acid, it is possible to improve the cell membrane permeability of the nucleic acid. The "$C_{2-10}$ perfluoroalkyl group which may have from 1 to 5 ether-bonding oxygen atoms between carbon atoms" consists of a "$C_{2-10}$ perfluoroalkyl group having from 1 to 5 ether-bonding oxygen atoms between carbon atoms" and a "$C_{2-10}$ perfluoroalkyl group having no ether-bonding oxygen atoms".

The "$C_{2-10}$ perfluoroalkyl group having from 1 to 5 ether-bonding oxygen atoms between carbon atoms" is the above-mentioned ether bond-containing perfluoroalkyl group. The introduction of said ether bond-containing perfluoroalkyl group into a nucleic acid can be carried out, as described above, by the phosphoramidite chemistry using a phosphoramidite containing an ether bond-containing perfluoroalkyl group.

The introduction of a $C_{2-10}$ perfluoroalkyl group which does not have an ether-bonding oxygen atom, into a nucleic acid can also be carried out in the same way by the phosphoramidite chemistry using a phosphoramidite containing a $C_{2-10}$ perfluoroalkyl group which does not have an ether-bonding oxygen atom. By other methods described in Non-Patent Documents 3 to 6, it is also possible to introduce a $C_{2-10}$ perfluoroalkyl group which does not have an ether-bonding oxygen atom, into a nucleic acid.

The $C_{2-10}$ perfluoroalkyl group which may have from 1 to 5 ether-bonding oxygen atoms between carbon atoms, may be introduced at any position of a nucleic acid so long as a perfluorinated structure is introduced into the nucleic acid. The position of the nucleic acid into which the $C_{2-10}$ perfluoroalkyl group is to be introduced, may be optionally determined to such an extent that the function of the nucleic acid will not be impaired.

A nucleic acid whose cell membrane permeability has been improved by the introduction of a $C_{1-20}$ perfluoroalkyl group that do not have ether-bonding oxygen atoms, is also desirable as an active ingredient in a nucleic acid drug, like a nucleic acid having an ether bond-containing perfluoroalkyl group introduced.

For a nucleic acid that has pharmacological activity but cannot reach into cells, by carrying out the method of improving the cell membrane permeability of the nucleic acid, it is possible to improve the uptake efficiency of the nucleic acid into the target cells. That is, by the method for improving the cell membrane permeability of the nucleic acid according to the present invention, it is possible to easily construct a drug delivery system for delivering the nucleic acid drug into cells.

EXAMPLES

In the following, the present invention will be described with reference to Examples, but the present invention is not limited to these Examples.

The NMR device used for the analyses in Examples and Comparative Examples was JNM-ECZ400S (400 MHz) manufactured by JEOL, and 0 PPM was used as the reference value for tetramethylsilane in $^{1}H$ NMR, and −162 PPM was used as the reference value for $C_6F_6$ in $^{19}F$ NMR.

<Tm Measurement>

In subsequent experiments, the melting temperature (Tm) of a nucleic acid was determined by measuring the change in absorbance at 260 nm as a function of temperature by using a UV-Vis spectrophotometer (UV-2550, manufactured by SHIMADZU). A melted sample was denatured at 100° C. and annealed slowly down to room temperature. The absorbance at 260 nm was measured and detected in 0.5° C. increments from 20° C. to 90° C. The concentration of double-stranded DNA was 4 μM in buffer (10 mM sodium phosphate, pH 7.0, 100 mM NaCl). Tm was calculated by the median method.

<Cell Culture>

In the following experiments, cell culture was conducted as follows.

HeLa cells were cultured in Dulbecco's modified Eagle's medium (DMEM, Thermo Fischer Scientific) supplemented with 10% FBS and 0.5% penicillin/streptomycin in a humidified atmosphere (5 volume % $CO_2$) at 37° C. Cells for image analysis were cultured in a 35 mm glass bottom dish (manufactured by IWAKI).

<Confocal Microscope Observation>

In subsequent experiments, confocal microscopy of cells was conducted as follows.

Fluorescein-conjugated N[PFC] or N[PFPE] (500 μM, 5 μL) was added to HeLa cells and incubated at 37° C. for 3 hours. Then, the nuclear staining agent, Hoechst 33342 (2 μg/m L, 0.5 mL), was added to the cells and further incubated for 1 hour. From each dish after incubation, the solution was removed and washed with PBS (-), and then DMEM (1 mL) was added. Then, each dish was placed in a confocal laser scanning microscope, and fluorescence images were acquired with an excitation wavelength of 488 nm and an emission filter of >505 nm.

<Flow Cytometry>

In subsequent experiments, flow cytometry was conducted as follows.

HeLa cells were seeded in 12-well plates at a density of $10^5$ cells/well and cultured. On the day after seeding, the medium in each well was replaced with DMEM medium (1 mL) containing DNA (2.5 μM) modified with fluorescein-bound N[PFC] or N[PFPE], and incubated for 4 or 24 hours. Then, the cell layer in the wells was washed twice with PBS, and the cells were detached by treatment with 0.05% (w/v) trypsin (200 μL) at 37° C. for 5 min. The recovered cells were suspended in DMEM (600 μL). The cell suspension was separated by centrifugation process (400G, 3 min), and PBS/1% BSA (500 μL) was added. The percentage of fluorescent cells and the average fluorescence intensity of this cell suspension were analyzed by a flow cytometer ("guava easyCyte8", manufactured by Luminex).

In the case of double-stranded DNA, a sample was denatured at 100° C. and annealed by slowly bringing it down to room temperature.

Example 1

A phosphoramidite containing a $C_5$ perfluoroalkyl group having 2 ether-bonding oxygen atoms ($CF_3CF_2O(CF_2)_2O(CF_2)$—; hereinafter referred to as a $C_5$-PFPE group), was synthesized and by using it, a nucleic acid containing the $C_5$-PFPE group was produced by the amidite method.

(1) Synthesis of $C_5$-PFPE Carboxylic Acid

A carboxylic acid salt containing a $C_5$-PFPE group was synthesized by the method described in Patent Document 4.

$CH_3CH_2O(CH_2)_2O(CH_2)_2OH$ (300 g) was put in a 2 L autoclave made of Hastelloy C. The reactor was cooled and under stirring in a closed state, $CF_3CF_2CF_2OCF(CF_3)CF_2OCF(CF_3)COF$ (1,339 g) was slowly introduced so that the internal temperature was maintained to be at most 30° C. After the total amount was introduced, stirring at 30° C. was further conducted for 3 hours, and then HF generated in the reaction was driven out of the system by bubbling nitrogen gas to obtain the product. As a result of GC (gas chromatography) analysis of the product, 99.6% of $CH_3CH_2O(CH_2)_2O(CH_2)_2OCOCF(CF_3)OCF_2CF(CF)_3OCF_2CF_2CF_3$ was formed, and no unreacted $CH_3CH_2O(CH_2)_2O(CH_2)_2OH$ was detected. This product was used in the next step without purification.

To a 500 mL nickel autoclave, R-113 (312 g) was added, then stirred and kept at 25° C. At the autoclave gas outlet, a cooler maintained at 20° C., a NaF pellet filling layer and a cooler maintained at −10° C. were installed in series. Further, from the cooler maintained at −10° C., a liquid return line was installed to return the flocculated liquid to the autoclave. After blowing nitrogen gas into the autoclave for 1 hour at room temperature, fluorine gas diluted to 20% with nitrogen gas (hereinafter referred to as 20% diluted fluorine gas) was added at a flow rate of 17.04 L/h at room temperature for 1 hour. Next, while blowing in the 20% diluted fluorine gas at the same flow rate, a solution having the product obtained above (10 g) dissolved in R-113 (150 g) was injected for 4.1 hours.

Then, the pressure in the autoclave was increased to 0.15 MPaG while blowing in the 20% diluted fluorine gas at the same flow rate. Nine mL of a R-113 solution having a benzene concentration of 0.01 g/mL was injected while the temperature was raised from 25° C. to 40° C. The benzene solution inlet of the autoclave was closed, and stirring was continued for 0.3 hour. Next, 6 mL of the above-mentioned benzene solution was injected while maintaining the pressure in the reactor at 0.15 MPaG and the temperature in the reactor at 40° C. The benzene solution inlet of the autoclave was closed, and stirring was continued for 0.3 hour. The same operation was repeated one more time. The total amount of benzene injected was 0.22 g, and the total amount of R-113 injected was 21 mL. Then, stirring was continued for one hour while further blowing in the 20% diluted fluorine gas at the same flow rate. Next, the pressure in the reactor was brought to ambient pressure, and nitrogen gas was blown in for 1 hour. The product was analyzed by $^{19}F$ NMR, and the result showed that the desired compound ($CF_3CF_2O(CF_2)_2O(CF_2)_2OCOCF(CF_3)OCF_2CF(CF)_3OCF_2CF_2CF_3$) was contained in 99% yield. Further, as a result of analyses by $^1H$ NMR and GC-MS, no compound having a C—H bond was identified.

Into a distillation column kettle (2 L capacity) equipped with a reflux condenser at 10° C., the above-obtained $CF_3CF_2O(CF_2)_2O(CF_2)_2OCOCF(CF_3)OCF_2CF(CF_3)OCF_2CF_2CF_3$ (4,273 g) was charged, and potassium fluoride (12.6 g) was added, followed by heating and stirring (heated medium temperature: 100 to 130° C.). The product was recovered by reaction distillation. As the main distillate, 1,273 g of the distillate with a purity of at least 99% was recovered. The boiling point was 66.5° C., and the yield was 84.5%. As a result of analyses of the fraction by $^1H$ NMR and GC-MS, no compound having a C—H bond was identified.

The obtained $CF_3CF_2O(CF_2)_2OCF_2COF$ (107 g) was charged in a 200 mL Hastelloy autoclave, and while stirring vigorously under ice-cold conditions, water (6 g) was slowly added dropwise for hydrolysis. After the dropwise addition, the temperature was gradually raised to room temperature, and stirring was further continued for 5 hours. After that, HF formed in the reaction was driven out of the system by bubbling nitrogen gas, and single distillation was continued to obtain 84 g of the fraction with a boiling point of 74° C./(30×133.322 Pa). The purity was 99.4%, and the yield was 79%.

(2) Synthesis of $C_5$-PFPE Alcohol

The $C_5$-PFPE carboxylic acid obtained in the above (1) was reduced to obtain an alcohol containing a $C_5$-PFPE group.

The carboxylate (17.3 g, 50 mmol) containing a $C_5$-PFPE group and anhydrous tetrahydrofuran (50 mL) were added to a three-necked flask equipped with a magnetic stirrer, a thermometer and a cooler. Then, sodium borohydride (2.84 g, 75 mmol) was added to said flask in an ice bath at less than 15° C., followed by further dropwise addition of boron trifluoride ether complex (9.42 mL, 75 mmol). The reaction mixture was refluxed for 24 hours and then cooled to 5° C., and distilled water was added until no gas was generated. The reaction mixture was then extracted three times with dichloromethane. All organic phases were combined and dried over anhydrous $Na_2SO_4$ and filtered, and then, the solvent was removed to obtain the alcohol as the target compound (67% yield).

(3) Synthesis of Trifluoromethanesulfonate

A trifluoromethanesulfonate containing a $C_5$-PFPE group was synthesized.

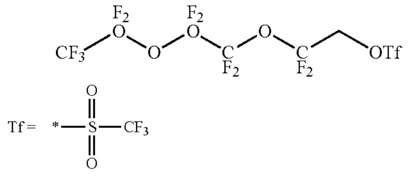

Fluorinated alcohol (4.98 g, 15.0 mmol) was dissolved in dry dichloromethane (75 mL), followed by addition of dry triethylamine (15 mL), and the mixture was cooled to −78° C. To this reaction solution, trifluoromethanesulfonic anhydride (6.34 g, 22.5 mmol) was added dropwise over 30 minutes, whereby the reaction mixture turned dark. This reaction mixture was stirred at 0° C. for 1 hour, then heated to room temperature and stirred for further 3 hours. The reaction was then stopped by adding saturated $NaHCO_3$. After the addition of $NaHCO_3$ (50 mL) to the reaction product, it was extracted three times with dichloromethane (50 mL). All organic phases were combined, washed with brine and dried over $MgSO_4$, and the solvent was removed under vacuum to obtain the desired compound as a dark black oily substance (27.3% yield). The obtained crude product was analyzed by $^1$H NMR and used in the next step without further purification.

$^1$H NMR (400 MHz, $CDCl_3$) δ4.70 (t, J=7.8 Hz, 2H). $^{19}$F NMR (376 MHz, $CDCl_3$) δ−74.1 (s, 3F), δ−77.6 (s, 2F), δ−86.6 (s, 3F), δ−88.2-88.7 (m, 6F).

(4) Diethanolamineation

The trifluoromethanesulfonate obtained in the above (3) was diethanolamineated.

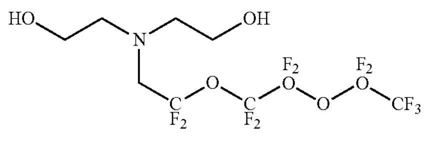

A solution of the trifluoromethanesulfonate (1.6 g, 3.5 mmol) obtained in the above (3) and diethanolamine (0.74 g, 7.0 mmol), was added to dry DMF (N,N-dimethylformamide) (5 mL). The obtained reaction mixture was put in an oil bath at 100° C. and stirred for 21 hours. The reaction mixture was then cooled and dissolved in water (20 mL), and the product was extracted three times with dichloromethane (20 mL). All the organic phases were combined, washed with brine and dried over $MgSO_4$, and the solvent was removed under vacuum to obtain the desired compound. The obtained crude product was analyzed by $^1$H NMR and used in the next step without further purification.

$^1$H NMR (400 MHz, $CDCl_3$) δ3.58 (t, J=5.0 Hz, 4H), δ3.24 (t, J=11.0 Hz, 2H), δ2.86 (t, J=5.5 Hz, 4H).

(5) DMTr Protection

One of the two hydroxy groups of the diethanolamine obtained in the above (4) was protected with DMTr (4,4'-dimethoxytriphenylmethyl group).

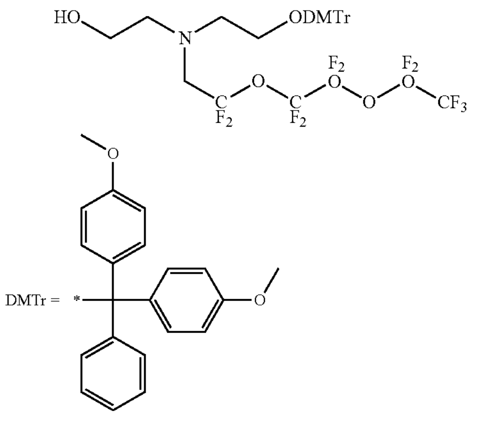

The diethanolamine (0.92 g, 2.2 mmol) obtained in the above (4) was dissolved in dry dichloromethane (7.5 mL) and triethylamine (1 mL). To this reaction mixture, DMTrCl (0.75 g, 2.2 mmol) was added little by little, and then the mixture was stirred at room temperature for 2 hours. Then, the solvent was removed from the reaction mixture under vacuum to obtain a dark brown oily substance. This oily substance was purified by column chromatography using a silica column pretreated with triethylamine and an EtOAc/hexane (volume ratio of 1:4) mixture to obtain the desired compound as a yellow oily substance (amount: 238 mg, yield: 15.2%).

$^1$H NMR (400 MHz, $CDCl_3$) δ7.40 (t, J=8.2 Hz, 2H), δ7.33-7.20 (m, 7H), δ6.82 (d, J=8.7 Hz, 4H), δ3.78 (s, 6H), δ3.50 (dd, J=5.5 Hz, 5.0 Hz, 2H), δ3.26-3.20 (m, 4H), δ2.93 (t, J=5.5 Hz, 2H), δ2.81 (t, J=5.0 Hz, 2H), δ2.44 (t, J=6.0 Hz, 1H). $^{19}$F NMR (376 MHz, $CDCl_3$) δ−73.6 (s, 2F), δ−86.5 (s, 3F), δ−88.3-88.4 (m, 4F), δ−88.6-88.7 (m, 2F).

(6) Synthesis of Phosphoramidites

In the diethanolamine obtained in the above (5) above, the hydroxy group not protected by the DMTr group was converted to an amidite.

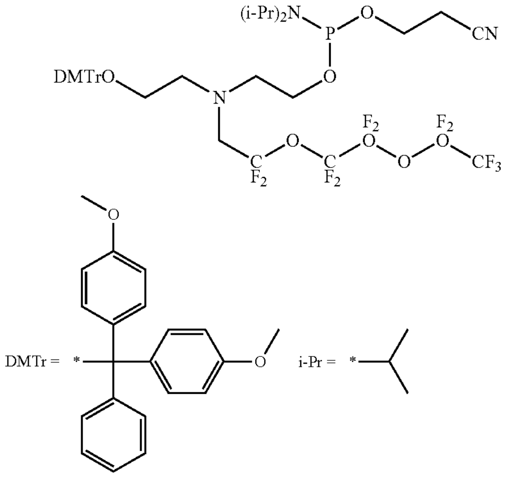

3-((Bis(diisopropylamino)phosphanyl)oxy)propanenitrile was dissolved in dry acetonitrile. To this reaction solution, 5-(ethylthiotetrazole) (ETT) (65 mg, 0.5 mmol) was added under argon, and then, a solution of the DMTr-protected diethanolamine (0.24 mg, 0.33 mmol) obtained in the above (5) dissolved in THF (1 mL) and acetonitrile (1 mL), was added little by little. The reaction mixture was then stirred for 4 hours at room temperature under argon, and then the solvent was evaporated under reduced pressure. The obtained crude product was purified by column chromatography with degassed hexane/ethyl acetate (volume ratio of 1:4) as mobile phase under argon, and the desired compound (N[$C_5$-PFPE]amidite) was isolated as a colorless oily substance (amount: 130 mg, yield: 43%).

$^1$H NMR (400 MHz, Acetone-$d_6$) δ7.45 (t, J=7.3 Hz, 2H), δ7.33-7.17 (m, 7H), δ6.85 (td, J=2.7 Hz, 9.1 Hz, 4H), δ3.84-3.56 (m, 6H), δ3.76 (s, 6H), δ3.50 (t, J=11.4 Hz, 2H), δ3.20 (t, 6.0 Hz, 2H), δ3.00 (t, J=5.5 Hz, 2H), δ2.95 (t, J=5.0 Hz, 2H), δ2.67 (t, J=6.0 Hz, 2H), δ1.16 (d, J=6.9 Hz, 6H), δ1.12 (d, J=6.9 Hz, 6H). $^{19}$F NMR (376 MHz, Acetone-$d_6$) δ−75.5 (m, 2F), δ−87.4 (s, 3F), δ−88.9 (m, 2F), δ−89.1 (m, 2F), δ−89.3 (m, 2F). $^{31}$P NMR (162 MHz, Acetone-$d_6$) δ−148.0 (m).

(7) DNA Synthesis

DNA synthesis was conducted by NTS H-8 DNA/RNA Synthesizer (manufactured by Nihon Techno Service Co., Ltd.) by using commercially available reagents, various phosphoramidites (acetonitrile solution, 0.1 M) and 5-ethylthio-1H-tetrazole (acetonitrile solution, 0.25 M) as activator.

The synthesis of 5'-N[$C_5$-PFPE]-modified DNA by bonding an N[$C_5$-PFPE] group to the 5'-end of an oligonucleotide consisting of sequence number 1 (5'-TTTTTCAGTTGACCATATA-3' (SEQ ID NO: 1)) was conducted as follows. First, DNA synthesis (tritylation off) by a 1,000 Å CPG solid support column (1 μmole scale), was conducted. Then, under a nitrogen atmosphere, by using a syringe, the N[$C_5$-PFPE] amidite (0.1 M acetonitrile solution, 300 μL) synthesized in the above (6) and an activator solution (300 μL) were mixed in the presence of CPG. After 5 minutes from the mixing, the solution was removed from the column, and strand capping, oxidation, and unblocking were conducted in a DNA synthesizer (11.0% yield).

5'-N[$C_5$-PFPE]-modified DNA

Sequence: 5'-(N[$C_5$-PFPE]) TTTTTCAGTTGACCATATA-3' (SEQ ID NO: 1) LRMS (MALDI) $[M-H]^-$: 6,245.0 (calcd), 6,244.2 (found)

The synthesis of 3'-N[$C_5$-PFPE]-modified DNA having an N[$C_5$-PFPE] group bonded to the 3'-end of an oligonucleotide consisting of sequence number 2 (5'-TATATGGTCAACTGAAAAA-3' (SEQ ID NO: 2)), which is the complementary base sequence to sequence number 1, was conducted as follows. First, under a nitrogen atmosphere, by using a syringe, the N[$C_5$-PFPE] amidite (0.1 M acetonitrile solution, 300 μL) synthesized in the above (4) and an activator solution (300 μL) were mixed in the presence of a 1,000 Å Glen UnySupport (registered trademark) (1 μmole scale). After 5 minutes from the mixing, the solution was removed from the column, and the strand capping, oxidation and unblocking were conducted by the DNA synthesizer. Then, a DNA oligomer was synthesized by the usual phosphoramidite chemistry using the DNA synthesizer (7.9% yield).

3'-N[$C_5$-PFPE]-modified DNA

Sequence: 5'-TATATGGTCAACTGAAAAA (N[$C_5$-PFPE])-3' (SEQ ID NO: 2) LRMS (MALDI) $[M-H]^-$: 6,321.1 (calcd), 6,321.3 (found)

Deprotection of the nucleic acid synthesized by the DNA synthesizer was carried out as follows. First, DNA (tritylation off) supported on CPG solid was treated with an ammonium hydroxide solution (28%) at 50° C. for 12 hours. Then, this crude product solution was separated from the solid support and concentrated at 30° C. under reduced pressure. The obtained concentrate was then filtered through a 0.45 μm centrifugal filter, followed by HPLC purification. The obtained solution was quantified by absorbance at 260 nm.

The HPLC purification was conducted under the following conditions. Solvent (0.45 μm centrifugally filtered): 100 mM triethylammonium acetate (TEAA) buffer (pH 7.0) and HPLC grade acetonitrile, elution gradient: 3-95% acetonitrile (40 min), column: COSMOSIL packed column "5C18-MS-II" (4.6 ID×150 nm, manufactured by Nacalai Tesque, Inc.), Sample crude DNA: a solution dissolved in 20 to 50 μL of ultrapure water was injected, Detection: absorbance at 260 nm was measured by a diode array detector.

The Tm values of the synthesized nucleic acids were measured. For the measurements of the Tm values, RNA with the base sequence corresponding to the DNA before the N[$C_5$-PFPE] modification, was used. The nucleic acids used for the measurements are shown in Table 1, and the results of the Tm value measurements are shown in Table 2.

TABLE 1

Table 1 discloses SEQ ID NOS 1, 1, 2, 2, and 1-4, respectively, in order of appearance.

| Name | Base sequence |
|---|---|
| FE1 | 5'-(N[$C_5$-PFPe])TTTTTCAGTTGACCATATA-3' |
| FE2 | 5'-(N[$C_5$-PFPe])$_2$TTTTTCAGTTGACCATATA-3' |
| rFE1 | 5'-TATATGGTCAACTGAAAAA-(N[$C_5$-PFPe])-3' |
| rFE2 | 5'-TATATGGTCAACTGAAAAA-(N[$C_5$-PFPe])$_2$-3' |
| cont-DNA | 5'-TTTTTCAGTTGACCATATA-3' |
| cont-rDNA | 5'-TATATGGTCAACTGAAAAA-3' |
| cont-RNA | 5'-UUUUUCAGUUGACCAUAUA-3' |
| cont-rRNA | 5'-UAUAUGGUCAACUGAAAAA-3' |

TABLE 2

| Sequence 1 | Sequence 2 | Tm |
|---|---|---|
| cont-DNA | cont-rDNA | 55.5° C. |
| FE1 | rFE1 | 56.5° C. |
| FE1 | cont-rDNA | 56.5° C. |
| cont-DNA | rFE1 | 55.1° C. |
| cont-DNA | cont-rRNA | 52.9° C. |
| FE1 | cont-rRNA | 56.8° C. |
| cont-RNA | cont-rDNA | 48.3° C. |
| cont-RNA | rFE1 | 49.5° C. |

The Tm value of N[$C_5$-PFPE]-modified DNA was almost the same as that of unmodified DNA. When annealed with RNA, the Tm value increased slightly.

Example 2

A phosphoramidite containing a $C_8$ perfluoroalkyl group ($-C_8F_{17}$: hereinafter referred to as a $C_8$-PFC group) not having an ether-bonding oxygen atom, was synthesized, and by using this, a nucleic acid containing the $C_8$-PFC group was produced by the amidite method.

A phosphoramidite containing the $C_8$-PFC group, represented by the following formula, was synthesized by the method described in Non-Patent Document 5.

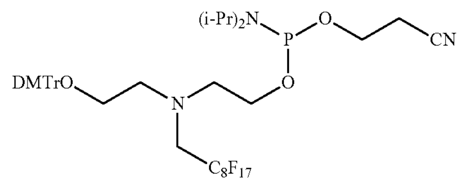

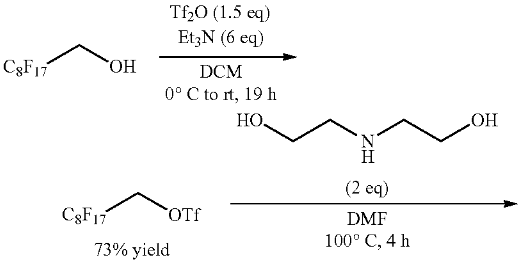

-continued

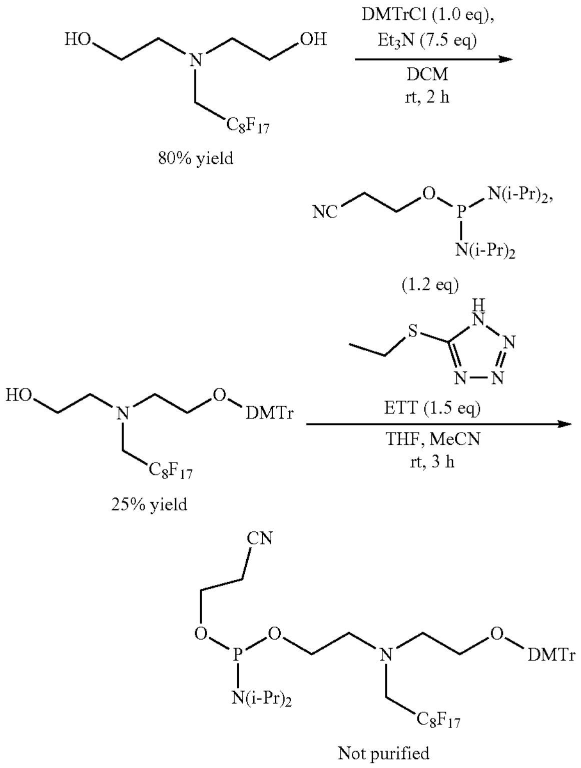

In the same manner as in Example 1 except that the obtained phosphoramidite containing the $C_8$-PFC group was used, a 5'-N[$C_8$-PFC]-modified DNA in which an N[$C_8$-PFC] group is bonded to the 5'-end of an oligonucleotide comprising sequence number 1 and a 3'-N[$C_8$-PFC]-modified DNA in which an N[$C_8$-PFC] group is bonded to the 3'-end of an oligonucleotide comprising sequence number 2, were synthesized.

The Tm values of the synthesized nucleic acids were measured. For the measurements of the Tm values, RNA with the base sequences corresponding to DNA before the N[$C_8$-PFC] modification, was used in the same manner as in Example 1. The nucleic acids used for the measurements are shown in Table 3, and the results of the Tm value measurements are shown in Table 4.

TABLE 3

Table 3 discloses "TTTTTCAGTTGACCATATA" as SEQ ID NO: 1 and "TATATGGTCAACTGAAAAA" as SEQ ID NO: 2.

| Name | Base sequence |
|---|---|
| F1 | 5'-(N[$C_5$-PFC])TTTTCAGTTGACCATATA-3' |
| F2 | 5'-(N[$C_5$-PFC])$_2$TTTTTCAGTTGACCATATA-3' |
| F5 | 5'-(N[$C_5$-PFC])$_5$TTTTTCAGTTGACCATATA-3' |
| rF1 | 5'-TATATGGTCAACTGAAAAA(N[$C_5$-PFC])-3' |
| rF2 | 5'-TATATGGTCAACTGAAAAA(N[$C_5$-PFC])$_2$-3' |
| rF5 | 5'-TATATGGTCAACTGAAAAA(N[$C_5$-PFC])$_5$-3' |

TABLE 4

| Sequence 1 | Sequence 2 | Tm |
|---|---|---|
| cont-DNA | cont-rDNA | 55.8° C. |
| F1 | rF1 | 59.0° C. |
| F2 | rF2 | 72.0° C. |
| F3 | rF3 | 79.9° C. |
| F1 | cont-rDNA | 57.6° C. |
| cont-DNA | rFE1 | 55.5° C. |
| F2 | cont-rDNA | 57.6° C. |
| cont-DNA | rFE2 | 56.7° C. |
| F5 | cont-rDNA | 50.6° C. |
| cont-DNA | rFE5 | 50.8° C. |
| cont-DNA | cont-rRNA | 52.9° C. |
| F1 | cont-rRNA | 57.5° C. |
| F2 | cont-rRNA | 54.6° C. |
| F5 | cont-rRNA | 48.5° C. |
| cont-RNA | cont-rDNA | 48.3° C. |
| cont-RNA | rF1 | 49.3° C. |
| cont-RNA | rF2 | 50.3° C. |
| cont-RNA | rF5 | 45.4° C. |

In a case where N[$C_8$-PFC]-modified DNA's were annealed with one another, the Tm value tended to increase as the number of N[$C_8$-PFC] introduced was increased. In a case where N[$C_8$-PFC]-modified DNA was annealed with DNA or RNA, the Tm value tended to be higher when two N[$C_8$-PFC] were introduced than when one N[$C_8$-PFC] was introduced, but when five N[$C_8$-PFC] were introduced, the Tm value was lower than that of DNA or RNA before modification.

Test Example 1

The nucleic acid having fluorescein bonded to the 3'-end of the N[$C_8$-PFC]-modified DNA synthesized in Example 2 was, as a single strand or as a double strand, added to the culture medium of HeLa cells and incubated, whereby the efficiency of cellular uptake was examined by flow cytometry.

Figure 1B:
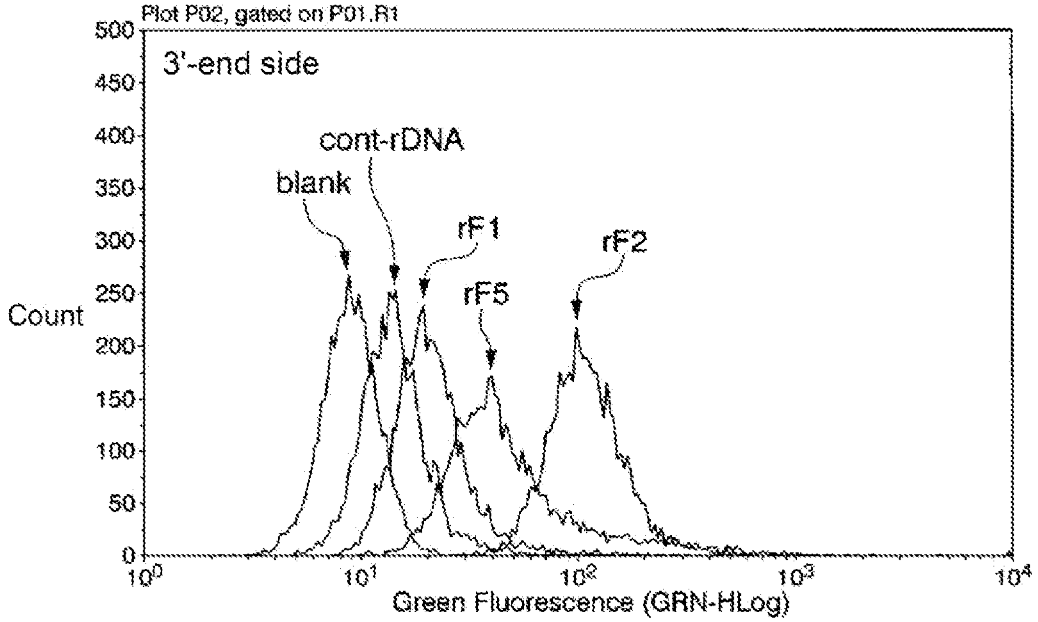
FIG. 1B is a graph showing the results of flow cytometry of cells having fluorescein-modified nucleic acids with N[$C_8$-PFC] modification at the 3'-end incorporated in Test Example 1.

FIG. 1A shows the results of flow cytometry of cells having fluorescein-modified nucleic acids of cont-DNA, F1, F2, and F5 incorporated, and FIG. 1B shows the results of flow cytometry of cells having fluorescein-modified nucleic acids of cont-rDNA, rF1, rF2, and rF5 incorporated. In the single-stranded nucleic acids with N[$C_8$-PFC] modification at the 3'-end, each of the N[$C_8$-PFC]-modified nucleic acids had a higher cellular uptake than the unmodified nucleic acid (cont-rDNA) (FIG. 1B). In the single-stranded nucleic acids with N[$C_8$-PFC] modification at the 5'-end, F1 having one N[$C_8$-PFC] introduced, had no difference from the fluorescein-modified nucleic acid of cont-DNA, but the fluorescein-modified nucleic acids of F2 and F5 having two or five N[$C_8$-PFC] introduced had a higher cellular uptake than the fluorescein-modified nucleic acid of cont-DNA (FIG. 1A).

Figure 2A:
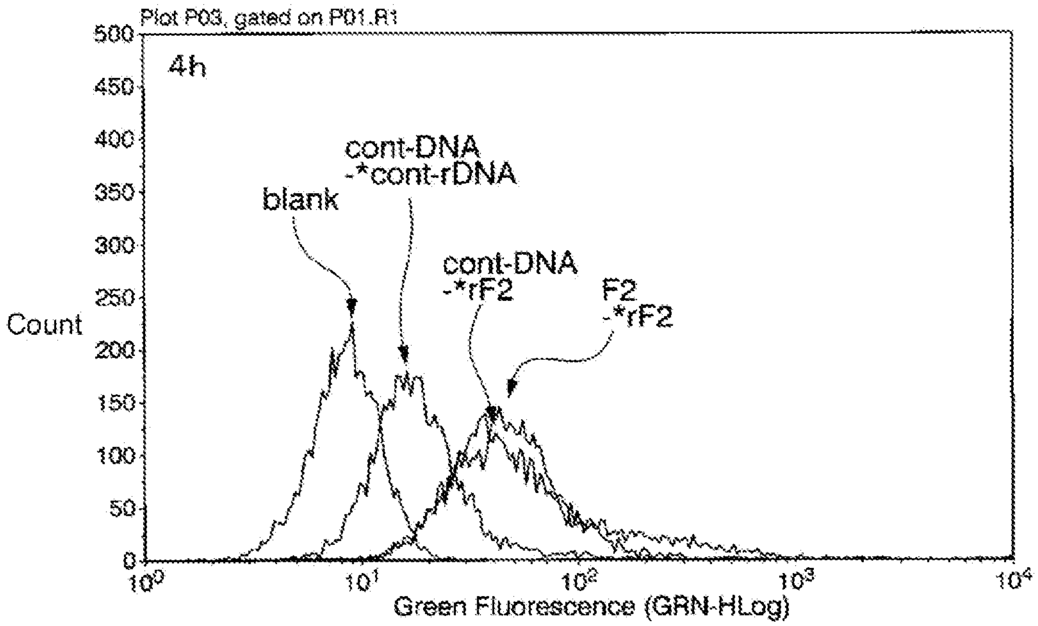
FIG. 2A is a graph showing the results of flow cytometry of cells having fluorescein-modified double-stranded nucleic acids annealed in each combination, incubated for 4 hours and incorporated in Test Example 1.
Figure 2B:
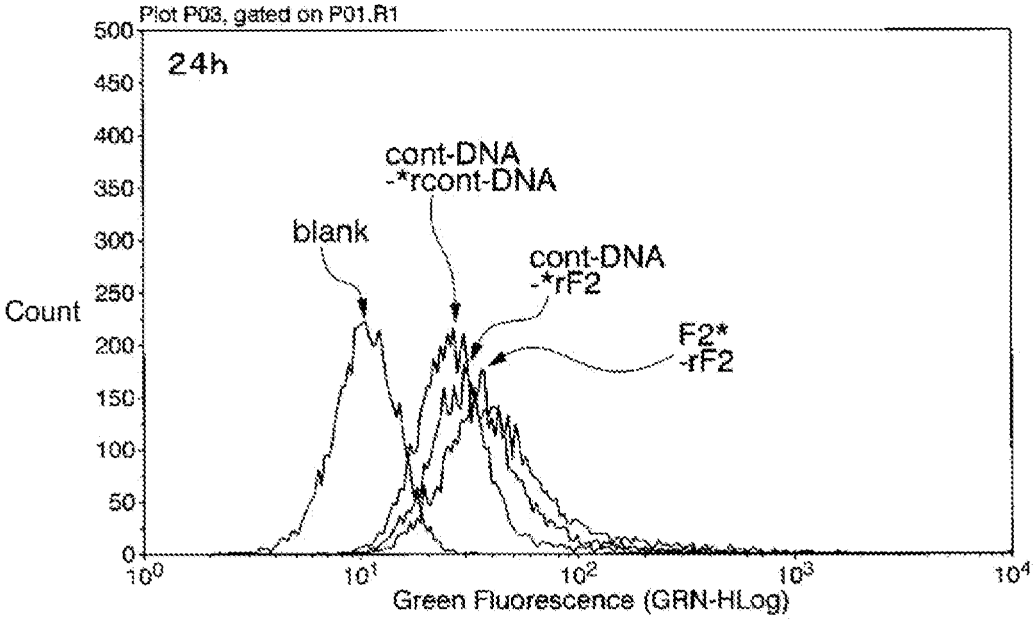
FIG. 2B is a graph showing the results of flow cytometry of cells having fluorescein-modified double-stranded nucleic acids annealed in each combination, incubated for 24 hours and incorporated in Test Example 1.

FIG. 2 shows the results of flow cytometry of cells that have taken up fluorescein-modified double-stranded nucleic acids annealed in each combination. FIG. 2A shows the results of cells incubated for 4 hours, and FIG. 2B shows the results of cells incubated for 24 hours. The double-stranded nucleic acid consisting of F2 and rF2 had the highest cellular uptake, and the double-stranded nucleic acid consisting of cont-DNA and rF2 had a higher cellular uptake than the double-stranded nucleic acid consisting of cont-DNA and cont-rDNA.

From these results, it has been found that by modifying nucleic acids with N[$C_8$-PFC], the amount of uptake into the cells will increase, and the uptake efficiency will be improved. Such an improvement in the cellular uptake efficiency is due to the improvement of the cell membrane permeability of the nucleic acid by the N[$C_8$-PFC] modification.

Test Example 2

The nucleic acid having fluorescein bonded to the 3'-end of the N[$C_5$-PFPE]-modified DNA synthesized in Example 1 was, as a single strand, added to the culture medium of HeLa cells and incubated, whereby the efficiency of cellular uptake was examined by flow cytometry.

Figure 3:
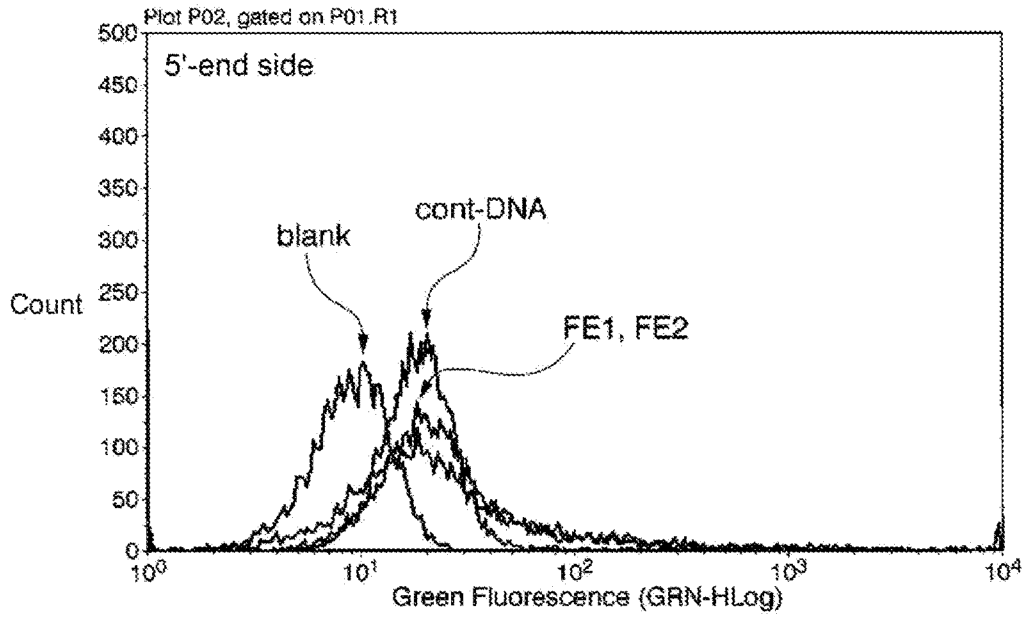
FIG. 3 is a graph showing the results of flow cytometry of cells having fluorescein-modified nucleic acids with N[$C_5$-PFPE] modification at the 5'-end incorporated in Test Example 2.

FIG. 3 shows the results of flow cytometry of cells having fluorescein-modified nucleic acids of cont-DNA, FE1 and FE2 incorporated. Each of single-stranded nucleic acids modified with N[$C_5$-PFPE] at the 5'-end, had a higher cellular uptake than unmodified nucleic acid (cont-rDNA).

In the same manner as described above, 5'-N[$C_5$-PFPE]-modified DNA having an N[$C_5$-PFPE] group bonded to the 5'-end of an oligonucleotide consisting of sequence number 1, was synthesized. The synthesized nucleic acids are shown in Table 5.

TABLE 5

Table 5 discloses "TTTTTCAGTTGACCATATA" as SEQ ID NO: 1.

| Name | Base sequence |
|---|---|
| FE5 | 5'-(N[$C_5$-PFPE])$_5$TTTTTCAGTTGACCATATA-3' |
| FE10 | 5'-(N[$C_5$-PFPE])$_{10}$TTTTTCAGTTGACCATATA-3' |

Figure 4:
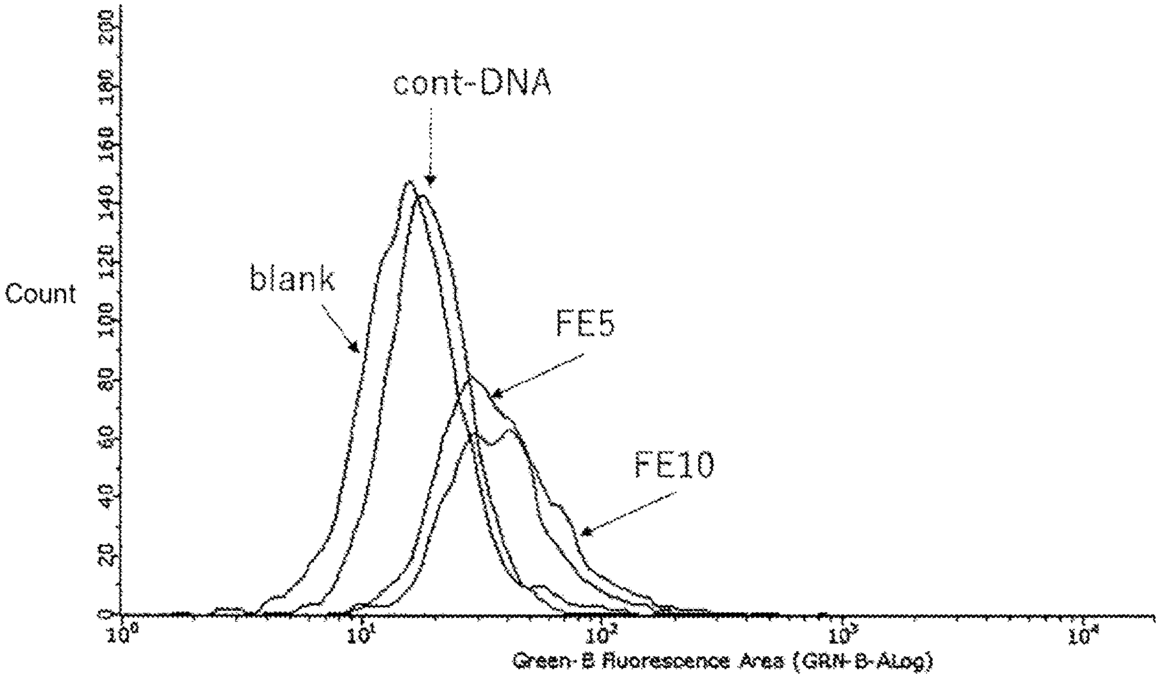
FIG. 4 is a graph showing the results of flow cytometry of cells having fluorescein-modified nucleic acids of cont-DNA, FE5 and FE10 incorporated in Test Example 2.

FIG. 4 shows the results of flow cytometry of cells having fluorescein-modified nucleic acids of cont-DNA, FE5, and FE10 incorporated. Each of the single-stranded nucleic acids modified with N[$C_5$-PFPE] at the 5'-end, had a higher cellular uptake than the unmodified nucleic acid (cont-rDNA).

Example 3

A phosphoramidite containing a $C_7$ perfluoroalkyl group ($CF_3CF_2O(CF_2)_2O(CF_2)_2O(CF_2)$—: hereinafter referred to as a $C_7$-PFPE group) having three ether-bonding oxygen atoms was synthesized, and by using this, a nucleic acid containing the $C_7$-PFPE group was produced by the amidite method.

(1) Synthesis of $C_7$-PFPE Carboxylic Acid

Using $CH_3CH_2(OCH_2CH_2)_3OH$ and $F(CF_2)_3OCF(CF_3)CF_2OCF(CF_3)COF$ as starting materials, $CF_3CF_2(OCF_2CF_2)_2OCF_2COF$ was obtained by the liquid-phase fluorination method and the KF pyrolysis method described in WO2000/056694.

The obtained $CF_3CF_2(OCF_2CF_2)_2OCF_2COF$ was used in the same way as the above-mentioned synthesis of the $C_5$-PFPE carboxylic acid to obtain $CF_3CF_2(OCF_2CF_2)_2OCF_2COOH$ ($C_7$-PFPE carboxylic acid).

(2) Synthesis of $C_7$-PFPE Alcohol

In the same manner as the synthesis of the $C_5$-PFPE alcohol as described above, $CF_3CF_2(OCF_2CF_2)_2OCF_2CH_2OH$ ($C_7$-PFPE alcohol) was obtained from the $C_7$-PFPE carboxylic acid.

(3) Synthesis of Trifluoromethanesulfonate

A trifluoromethanesulfonate containing a $C_7$-PFPE group was synthesized.

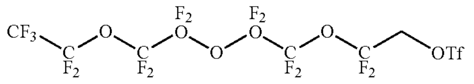

The above-mentioned $C_7$-PFPE alcohol (11.2 g, 25.0 mmol) was dissolved in water (5 mL), and then triethylamine (5 mL) was added, followed by cooling to 0° C. To this reaction mixture, trifluoromethanesulfonic acid chloride (4.42 g, 26.3 mmol) was added dropwise over 30 minutes. The reaction mixture was stirred at room temperature for 1.5 hours. The product was extracted three times with dichloromethane (10 mL). All the organic phases were combined, washed with brine and then dried over $MgSO_4$, and the solvent was removed under vacuum to obtain the desired compound as an oily substance. The obtained crude product was analyzed by $^1$H NMR and used in the next step without further purification. (Yield: 64%)

$^1$H NMR (400 MHz, $CDCl_3$) δ4.67 (t, J=8.2 Hz, 2H), $^{19}$F NMR (376 MHz, $CDCl_3$) δ−74.1 (s, 3F), δ−77.7 (s, 2F), δ−86.6 (s, 3F), δ−88.4-88.7 (m, 10F)

(4) Diethanolamineation

The trifluoromethanesulfonate containing the $C_7$-PFPE group obtained in the above (3) was diethanolamineated.

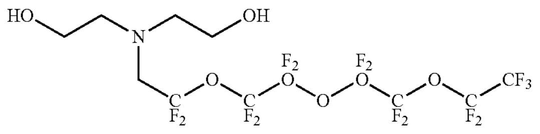

A solution of the trifluoromethanesulfonate (9.3 g, 16 mmol) containing the $C_7$-PFPE group obtained in the above (3) and diethanolamine (3.36 g, 32 mmol), was added to dry DMF (N,N-dimethylformamide) (12 mL). The obtained reaction mixture was put in an oil bath at 100° C. and stirred for 15 hours. The reaction mixture was then cooled and dissolved in water (20 mL), and the product was extracted three times with dichloromethane (20 mL). All the organic phases were combined, washed with brine and dried over $MgSO_4$, and the solvent was removed under vacuum to obtain the desired compound. The obtained crude product was analyzed by $^1$H NMR and used in the next step without further purification.

$^1$H NMR (400 MHz, $CDCl_3$) δ3.34 (m, 4H), δ3.09 (dt, J=2.3, 11.0 Hz, 2H), δ2.68 (m, 4H), $^{19}$F NMR (376 MHz, $CDCl_3$) δ−74.0 (s, 2F), δ−87.4 (s, 3F), δ−89.0-89.6 (m, 10F)

(5) DMTr Protection

One of the two hydroxy groups of the diethanolamine containing the $C_7$-PFPE group obtained in the above (4) was protected with DMTr (4,4'-dimethoxytriphenylmethyl group).

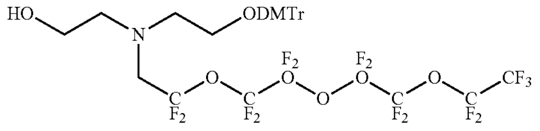

The diethanolamine (6.58 g, 12.3 mmol) containing the $C_7$-PFPE group obtained in the above (4) was dissolved in dry dichloromethane (20 mL) and triethylamine (6 mL). To this reaction mixture, DMTrCl (4.58 g, 13.5 mmol) was added little by little, and then the mixture was stirred at room temperature for 2 hours. Then, the solvent was removed from the reaction mixture under vacuum to obtain a dark brown oily substance. This oily substance was purified by column chromatography using a silica column pretreated with triethylamine and an EtOAc/hexane (volume ratio of 1:4) mixture to obtain the desired compound as a yellow oily substance (37% yield).

$^{1}H$ NMR (400 MHz, $CDCl_3$) δ7.41 (d, J=7.3 Hz, 2H), δ7.33-7.15 (m, 7H), δ6.81 (dt, J=9.1, 3.7 Hz, 4H), δ3.78 (s, 6H), δ3.50 (dd, J=6.0 Hz, 10.8 Hz, 2H), δ3.24-3.19 (m, 4H), δ2.91 (t, J=5.5 Hz, 2H), δ2.79 (t, J=5.0 Hz, 2H), δ2.43 (t, J=6.0 Hz, 1H) $^{19}F$ NMR (376 MHz, $CDCl_3$) δ−74.4 (m, 2F), δ−86.7 (s, 3F), δ−88.1-88.6 (m, 10F)

(6) Synthesis of Phosphoramidites

Of the diethanolamine containing the $C_7$-PFPE group obtained in the above (5), the hydroxyl group not protected by the DMTr group was converted to an amidite.

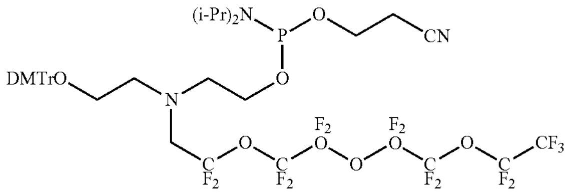

3-((Bis(diisopropylamino)phosphanyl)oxy)propanenitrile (1.76 g, 5.9 mmol) was dissolved in dry acetonitrile. To this reaction solution, 5-(ethylthiotetrazole) (ETT) (7.61 g, 5.9 mmol) was added under argon, and then, a solution having the DMTr-protected diethanolamine (3.26 g, 3.9 mmol) containing the $C_7$-PFPE group obtained in the above (5) dissolved in THF (5 mL) and acetonitrile (5 mL), was added little by little. This reaction mixture was then stirred for 4 hours at room temperature under argon. The solvent was evaporated under reduced pressure. The obtained crude product was purified by column chromatography under argon using degassed hexane/ethyl acetate (volume ratio of 1:4) as the mobile phase, whereby the desired compound (N[$C_7$-PFPE]amidite) was isolated as a colorless oily substance (78% yield).

$^{1}H$ NMR (400 MHz, Acetone-$d_6$) δ7.41 (d, J=8.7 Hz, 2H), δ7.32-7.14 (m, 7H), δ6.83-6.79 (m, 4H), δ3.80-3.51 (m, 6H), δ3.77 (s, 6H), δ3.50 (t, J=11.4 Hz, 2H), δ3.25 (t, 11.4 Hz, 2H), δ3.15 (t, J=6.0 Hz, 2H), δ2.94-2.89 (m, 4H), 2.54 (t, J=6.4 Hz, 2H), δ1.16 (d, J=6.9 Hz, 6H), δ1.12 (d, J=6.9 Hz, 6H), $^{19}F$ NMR (376 MHz, Acetone-$d_6$) δ−75.0 (m, 2F), δ−86.6 (s, 3F), δ−88.3-88.8 (m, 10F), $^{31}P$ NMR (162 MHz, Acetone-$d_6$), δ−148.4 (s)

5'-N[$C_7$-PFPE]-modified DNA having an N[$C_7$-PFPE] group bonded to the 5'-end of an oligonucleotide consisting of sequence number 1, was synthesized.

The synthesis of the 5'-N[$C_7$-PFPE]-modified DNA having an N[$C_7$-PFPE] group bonded to the 5'-end of an oligonucleotide consisting of sequence number 1, was conducted as follows. First, a DNA synthesis (tritylation off) on a 1,000 Å CPG solid support column (1 μmole scale) was conducted. Then, under a nitrogen atmosphere, using a syringe, the N[$C_7$-PFPE]amidite (0.1 M acetonitrile solution, 300 μL) synthesized in the above (6) and an activator solution (300 μL) were mixed in the presence of CPG. After 5 minutes from the mixing, the solution was removed from the column, and strand capping, oxidation and unblocking were conducted in a DNA synthesizer.

Deprotection and HPLC purification of nucleic acids were conducted in the same manner as described above. The synthesized nucleic acids are shown in Table 6.

TABLE 6

Table 6 discloses "TTTTTCAGTTGACCATATA" as SEQ ID NO: 1.

| Name | Base sequence |
|---|---|
| FE(2)1 | 5'-(N[$C_7$-PFPE])TTTTTCAGTTGACCATATA-3' |
| FE(2)2 | 5'-(N[$C_7$-PFPE])$_2$TTTTTCAGTTGACCATATA-3' |
| FE(2)5 | 5'-(N[$C_7$-PFPE])$_5$TTTTTCAGTTGACCATATA-3' |

Figure 5:
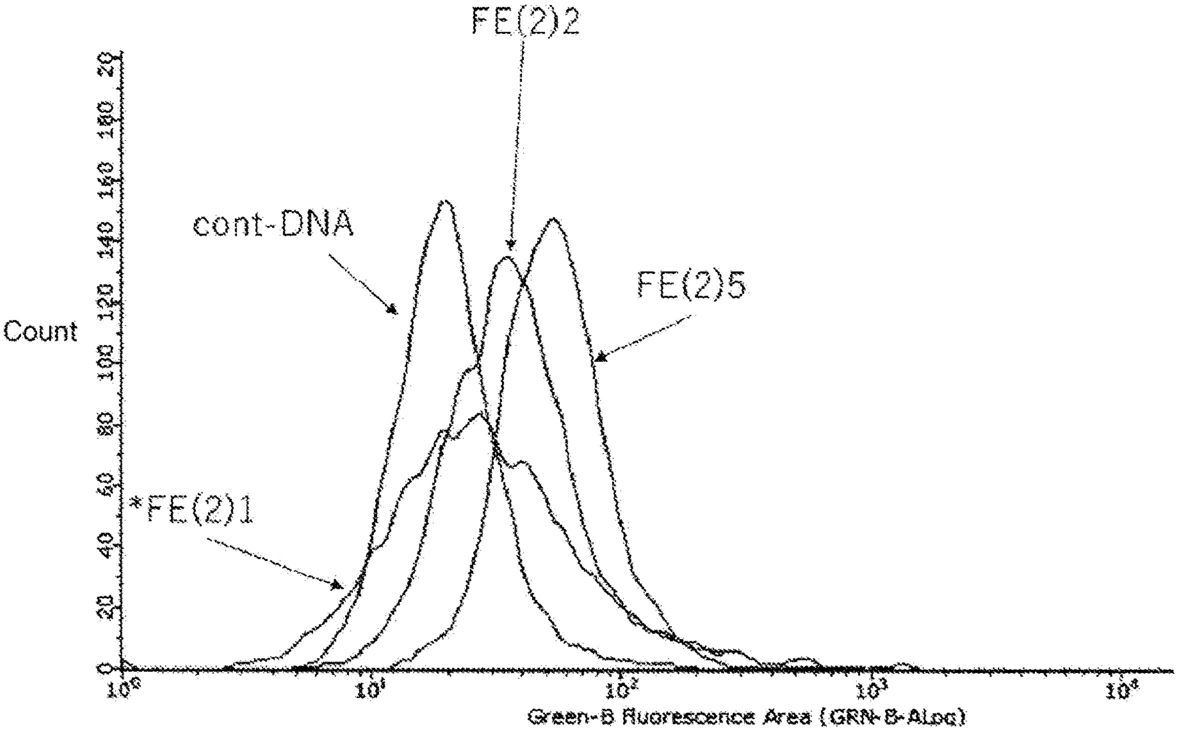
FIG. 5 is a graph showing the results of flow cytometry of cells having fluorescein-modified nucleic acids of cont-DNA, FE(2)1, FE(2)2 and FE(2)5 incorporated in Test Example 3.

FIG. 5 shows the results of flow cytometry of cells having fluorescein-modified nucleic acids of cont-DNA, FE(2)1, FE(2)2 and FE(2)5 incorporated. Each of the single-stranded nucleic acids modified by N[$C_7$-PFPE] at the 5'-end, had a higher cellular uptake than the unmodified nucleic acid (cont-rDNA).

Example 4

A phosphoramidite containing a $C_4$ perfluoroalkyl group (—$C_4F_9$; hereinafter referred to as a $C_4$-PFC group) not having an ether-bonding oxygen atom, was synthesized, and by using this, nucleic acids containing the $C_4$-PFC group were produced by the amidite method.

(1) Synthesis of Trifluoromethanesulfonate

A trifluoromethanesulfonate containing a $C_4$-PFC group was synthesized.

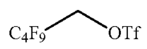

A fluorinated alcohol ($C_4F_9CH_2OH$) (500 mg, 2.0 mmol) was dissolved in dry dichloromethane (1 mL), then dry triethylamine (1 mL) was added, and the mixture was cooled to −78° C. To this reaction solution, trifluoromethanesulfonic anhydride (8.46 g, 3 mmol) was added dropwise over 30 min, whereby the reaction mixture turned dark. The reaction mixture was stirred at 0° C. for 1 hour, then heated to room temperature and further stirred for 18 hours. Then, the reaction was stopped by adding saturated $NaHCO_3$ (10 mL), followed by extraction three times with dichloromethane (50 mL). All organic phases were combined, washed with brine and dried over $MgSO_4$, and the solvent was removed under vacuum to obtain the desired compound as a dark black oily substance. The obtained crude product was analyzed by $^{1}H$ NMR and used in the next step without further purification. (61% yield).

$^{1}H$ NMR (400 MHz, $CDCl_3$) δ4.91 (t, J=12.3 Hz, 2H), $^{19}F$ NMR (376 MHz, $CDCl_3$) δ−74.3 (s, 3F), δ−81.2 (s, 3F), δ−120.1 (s, 2F), δ−124.0 (s, 2F), δ−126.4 (s, 2F).

(2) Diethanolamineation

The trifluoromethanesulfonate containing the $C_4$-PFC group obtained in the above (1) was diethanolamineated.

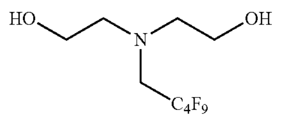

A solution of the trifluoromethanesulfonate containing the $C_4$-PFC group (459 mg, 1.2 mmol) obtained in the above (1) and diethanolamine (254 mg, 2.4 mmol) was added to dry DMF (5 mL). The obtained reaction mixture was put in an oil bath at 100° C. and stirred for 18 hours. Then, the reaction mixture was cooled and dissolved in water (10 mL), and the product was extracted three times with dichloromethane (20 mL). All the organic phases were combined, washed with brine and dried over $MgSO_4$ and the solvent was removed under vacuum to obtain the desired compound. The obtained crude product was analyzed by $^1$H NMR and used in the next step without further purification.

$^1$H NMR (400 MHz, $CDCl_3$) δ3.61 (t, J=5.0 Hz, 4H), δ3.21 (t, J=17.4 Hz, 2H), δ2.89 (t, J=5.5 Hz, 4H), $^{19}$F NMR (376 MHz, $CDCl_3$) δ−81.2 (s, 3F), δ−117.0 (s, 2F), δ−124.7 (s, 2F), δ−126.2 (s, 2F)

(3) DMTr Protection

One of the two hydroxyl groups of the diethanolamine containing the $C_4$-PFC group obtained in the above (2) was protected with DMTr (4,4'-dimethoxytriphenylmethyl group).

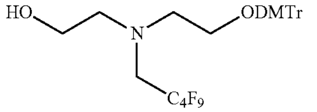

The diethanolamine (3.20 g, 9.5 mmol) containing the $C_4$-PFC group obtained in the above (2) was dissolved in dry dichloromethane (20 mL) and triethylamine (5 mL). To this reaction mixture, DMTrCl (3.21 g, 9.5 mmol) was added little by little, and then the mixture was stirred at room temperature for 2.5 hours. Then, the solvent was removed from the reaction mixture under vacuum to obtain a dark brown oily substance. This oily substance was purified by column chromatography using a silica column pretreated with triethylamine and an EtOAc/hexane (volume ratio of 1:4) mixture to obtain the desired compound as a yellow oily substance (54% yield).

$^1$H NMR (400 MHz, $CDCl_3$) δ7.41 (d, J=7.3 Hz, 2H), δ7.33-7.18 (m, 7H), δ6.82 (d, J=9.2 Hz, 4H), δ3.78 (s, 6H), δ3.52 (dd, J=5.5 Hz, 10.5 Hz, 2H), δ3.31 (t, J=16.9 Hz, 2H), δ3.23 (t, J=5.5 Hz, 2H) δ2.94 (t, J=5.5 Hz, 2H), δ2.81 (t, J=5.0 Hz, 2H), δ2.44 (t, J=6.2 Hz, 1H) $^{19}$F NMR (376 MHz, $CDCl_3$) δ−79.9 (s, 3F), δ−117.1 (s, 2F), δ−125.0 (s, 2F), δ−125.9 (s, 2F)

(4) Synthesis of Phosphoramidites

Of the diethanolamine containing the $C_4$-PFC group obtained in the above (3), the hydroxyl group not protected by the DMTr group was converted to an amidite.

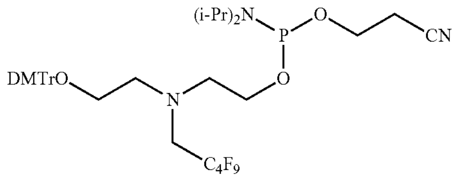

3-((Bis(diisopropylamino)phosphanyl)oxy)propanenitrile (1.84 g, 6.1 mmol) was dissolved in dry acetonitrile. To this reaction solution, 5-(ethylthiotetrazole) (ETT) (1.05 g, 7.7 mmol) was added under argon, and then, a solution having the DMTr-protected diethanolamine (3.26 g, 5.1 mmol) containing the $C_4$-PFC group obtained in the above (3) dissolved in THF (5 mL) and acetonitrile (5 mL), was added little by little. Then, the reaction mixture was stirred for 4 hours at room temperature under argon, and then the solvent was evaporated under reduced pressure. The obtained crude product was purified by column chromatography under argon using degassed hexane/ethyl acetate (volume ratio of 1:4) as the mobile phase, whereby the desired compound (N[$C_4$-PFC]amidite) was isolated as a colorless oily substance (45% yield).

$^1$H NMR (400 MHz, Acetone-$d_6$) δ7.41 (t, J=8.7 Hz, 2H), δ7.33-7.17 (m, 7H), δ6.85 (td, J=2.3 Hz, 8.7 Hz, 4H), δ3.84-3.56 (m, 6H), δ3.76 (s, 6H), δ3.37 (t, J=16.5 Hz, 2H), δ3.20 (t, 6.0 Hz, 2H), δ2.94 (t, J=5.5 Hz, 2H), δ2.90 (t, J=6.4 Hz, 2H), δ2.56 (t, J=6.4 Hz, 2H), δ1.16 (dd, J=6.9 Hz, 6H), δ1.12 (d, J=6.9 Hz, 6H), $^{19}$F NMR (376 MHz, Acetone-$d_6$), δ−80.9 (m, 2F), δ−117.7 (s, 2F), δ−124.3 (s, 2F), δ−126.0 (s, 2F), $^{31}$P NMR (162 MHz, Acetone-$d_6$), δ−148.4 (s)

INDUSTRIAL APPLICABILITY

The present invention provides a nucleic acid containing a perfluoroalkyl group and a method for its production. Since the nucleic acid of the present invention has excellent cell membrane permeability, it is expected to be used in the pharmaceutical field as a bioactive substance, for example, as a carrier for introducing medicinal ingredients into target cells.

What is claimed is:

1. A nucleic acid comprising a structure represented by the following general formula (A1):

(A1)

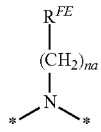

wherein $R^{FE}$ is a $C_{2-10}$ perfluoroalkyl group having from 1 to 5 ether-bonding oxygen atoms between carbon atoms of the perfluoroalkyl group, na is an integer of from 1 to 10, and the black dots represent the bonding hands.

2. The nucleic acid according to claim 1, wherein the perfluoroalkyl group is indirectly bonded to the 5'- or 3'-end of the nucleic acid.

3. The nucleic acid according to claim 1, wherein the perfluoroalkyl group is indirectly bonded between two nucleotides.

4. The nucleic acid according to claim 1, which is a cell membrane-permeable nucleic acid.

5. A method for producing a nucleic acid containing a perfluoroalkyl group, in which a compound represented by the following general formula (A2) is used as a raw material, and a nucleic acid containing a perfluoroalkyl group as defined in claim 1 is synthesized using phosphoramidite chemistry:

(A2)

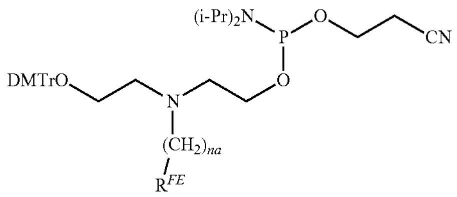

provided that the groups in the formula mean the following:

$R^{FE}$ is a $C_{2-10}$ perfluoroalkyl group having from 1 to 5 ether-bonding oxygen atoms between carbon atoms, na is an integer of from 1 to 10, DMTr is a 4,4'-dimethoxytriphenylmethyl group, and i-Pr is an isopropyl group.

6. A nucleic acid medicine containing, as the active ingredient, the nucleic acid according to claim 1.

* * * * *